Figure 12:
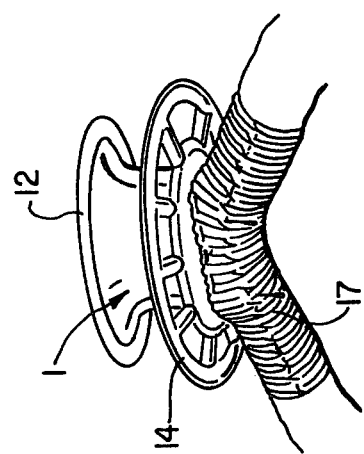

United States Patent [19]

Ivan et al.

[11] 4,306,545
[45] Dec. 22, 1981

[54] RE-ENTRANT CANNULA DEVICE

[75] Inventors: Michael Ivan, Nepean; Douglas W. Johnston, Ottawa, both of Canada

[73] Assignee: Canadian Patents & Development Limited, Ottawa, Canada

[21] Appl. No.: 171,169

[22] Filed: Jul. 22, 1980

[51] Int. Cl.³ ............................................. A61B 19/00
[52] U.S. Cl. .................................... 128/1 R; 128/274; 128/334 C
[58] Field of Search ............................ 128/348, 1, 274; 251/334 C, 334 R, 315

[56] References Cited

U.S. PATENT DOCUMENTS

| 3,704,704 | 12/1972 | Gonzales | 128/1 R |
| 3,707,957 | 1/1973 | Bucalo | 128/1 R |
| 3,880,137 | 4/1975 | Bucalo | 128/1 R |
| 4,169,477 | 10/1977 | Bokros | 128/334 R |

*Primary Examiner*—Stephen C. Pellegrino
*Attorney, Agent, or Firm*—Francis W. Lemon

[57] ABSTRACT

A re-entrant cannula device for use in the proximal duodenum and/or the site to terminal ileum of, for example, sheep and pigs, which comprises a casing of resilient material and a cylindrical plug cock which is pressed into the casing and has two digesta passages extending through the cylindrical plug cock along separate, isolated, curved paths. The casing has two, splayed intestine connectors and the cylindrical plug cock is rotated, by a connector tube in one digesta passage, from a "maintenance" position wherein digesta flows through one connector, along one digesta passage in the cylindrical plug cock and back to the intestine through the other connector, to a "collection" position where digesta flows from one connector along one digesta passage for collection and is returned to the intestine along the other digesta passage and connector back to the intestine.

3 Claims, 15 Drawing Figures

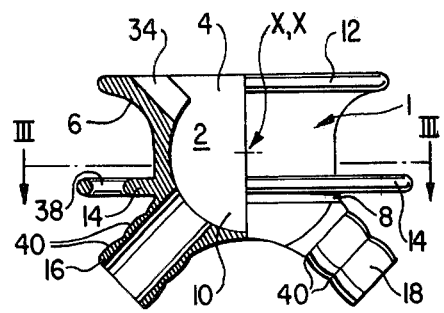
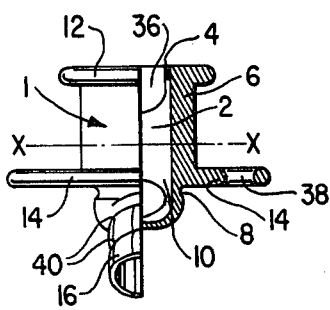
FIG.1  FIG.2
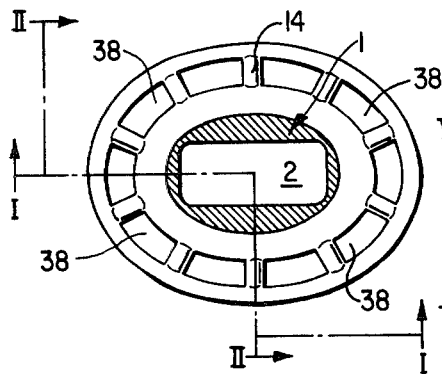
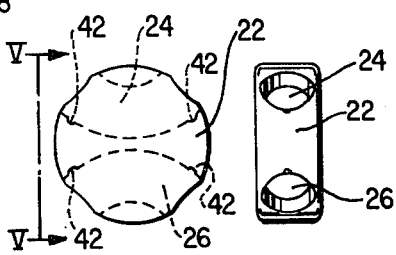
FIG.3  FIG.4  FIG.5
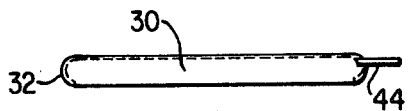
FIG.7
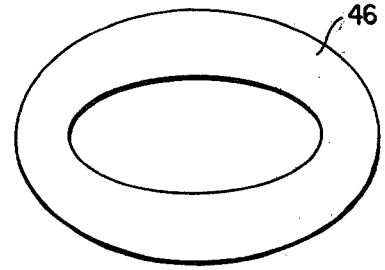
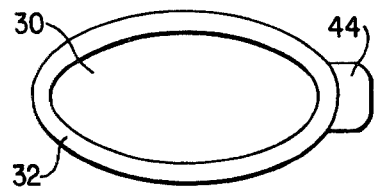
FIG.8
FIG.9
FIG.6

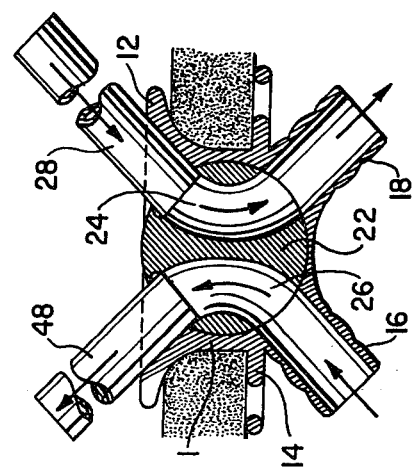
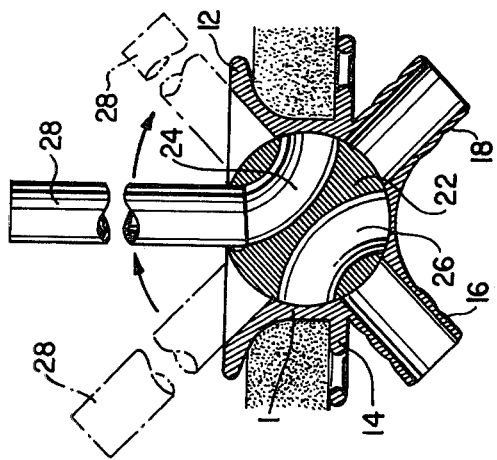
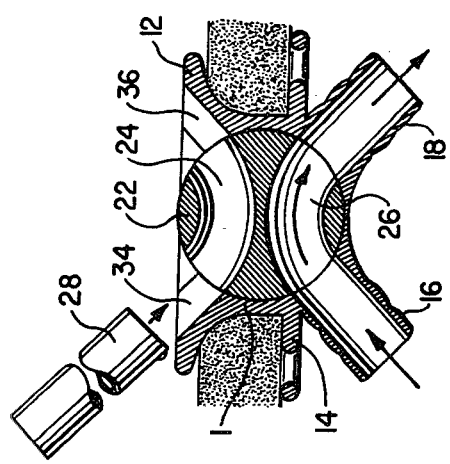

RE-ENTRANT CANNULA DEVICE

This invention relates to a re-entrant cannula device.

Re-entrant cannulation of the small intestine in sheep has been widely used in studies of the digestive process in ruminant and monogastric animals. Several types of cannula devices for sheep and corresponding surgical methods have been proposed wherein the cannula device is either T-shaped or have a curved barrel to divert digesta to a collection point outside the body and then provided for its re-entry by a further, similar cannula device. Two cannulas, drawn apart and connected with a plastic tube, are therefore required for the re-entrant system. The surgical procedures required intestinal transection and an incision of the mesentery under the transection so that the two cannula devices could be drawn apart and exteriorized through the abdominal wall. Since the mesentery was very short the re-entrant cannulation of the proximal duodenum by these cannula devices is complicated. In addition, maintenance of the external portion of the re-entrant cannula system is difficult and leakage of digesta usually develops within 2 to 4 weeks after surgery.

Some of the problems associated with the above mentioned cannula devices have been resolved by a more recent type of cannula device for pigs described by one of the applicants in "A New Type Of Re-Entrant Cannula Designed For Use In Small Intestine Of The Pig", M. Ivan, Australian Veterinary Journal Vol. 50, December, 1975, pages 547 to 552, which was later modified for use in the re-entrant cannulation of the duodenum in sheep as described by one of the applicants in "A New Method For Re-Entrant Cannulation Of The Duodenum In Sheep", M. Ivan, 1977, Canadian Journal of Animal Science, Vol. 57 pages 225 to 227. The cannula devices described in these papers are T-shaped in design and interchangeable into re-entrant system through the use of different "maintenance" and "collection" plugs. The insertion of the cannula device into the duodenum was achieved through one incision of the antimesenteric side and the duodenum was attached to the cannula by the use of a straight arterial graft of a polyester material. Although these cannula devices have been used successfully in the duodenum, their use in the terminal ileum of sheep has been found to be limited due to frequent blockage of channels in the "collection" plug.

There is a need for a cannula device, for the collection of digesta, which can easily be opened into a re-entrant system and wherein the problems of blockage and leakage of digesta are minimized.

According to the present invention there is provided a re-entrant cannula device, comprising:

(a) a casing, of a non-toxic, resilient material, with a plug cock cavity open at one side to a frontal portion of the casing and an external, purse string groove extending around an intermediate portion of the plug cock cavity, the casing having a frontal flange bounding the open side of the plug cock cavity and extending laterally therefrom around the frontal portion and being for frontal retention of skin and abdominal wall, an inner, perforated flange, the inner flange being inwardly spaced from the frontal portion and extending laterally in the same direction as and substantially parallel to the frontal flange and closer thereto than the purse string groove and extending around an intermediate portion of the plug cock cavity for adhesion to the internal side of the abdominal wall, and two intestine connectors inwardly spaced from the purse string groove, the intestine connectors being splayed and for conveying intestine digesta to and from the plug cock cavity.

(b) a cylindrical plug cock, of a non-toxic material for pressing into the plug cock cavity through the open side thereof and being rotatably retained therein for rotation about an axis extending across the plug cock cavity between the two intestine connectors, the plug cock having two intestine digesta conveying passages extending therethrough along separate, isolated, curved paths for alignment with the two intestine connectors so that rotation of the plug cock in the plug cock cavity will position the plug cock therein for, (i) in a first position the flow of digesta along only one of the passages between the two intestine connectors while one end of the other passage is accessible through the open side of the plug cock cavity, and (ii) in a second position the flow of digesta along one passage from one of the intestine connectors and the flow of digesta along the other passage to the other intestine connector, and (c) two substantially rigid connector tubes of a non-toxic material for placement to extend through the open side of the plug cock cavity with end portions of the connector tube releasably secured in end portions of the passages in the plug cock, at least one of which connector tubes may be used to rotate the plug cock between the said first and second positions.

Preferably a closure cap of a non-toxic material and having a beaded rim for press-fitting over the frontal flange to seal the plug cock cavity is provided.

In the accompanying drawings which illustrate, by way of example, an embodiment of the present invention, FIG. 1 is a partly sectioned side view, along I—I, FIG. 3, of a rotary valve casing of a re-entrant cannula device.

FIG. 2 is a partly sectioned end view, along II—II, FIG. 3, of the re-entrant cannula device shown in FIG. 1, FIG. 3 is a sectional plan view along III—III, FIG. 1, FIG. 4 is a side view of a cylindrical plug cock for the rotary valve casing shown in FIG. 1, FIG. 5 is an end view along V—V, FIG. 4

FIG. 6 is a side view of one of two identical connector tubes for the plug cock shown in FIG. 4, FIG. 7 is a side view of a closure cap for the rotary valve casing shown in FIG. 1, FIG. 8 is a bottom view of the closure cap shown in FIG. 7, FIG. 9 is a plan view of a removable collar for the rotary valve casing shown in FIG. 1, FIGS. 10 to 12 are perspective views of the surgical proceedure for inserting the re-entrant cannula device shown in FIGS. 1 to 8 into the intestine of a sheep, and FIGS. 13 to 15 are sectional side views showing the operation of the re-entrant cannula device shown in FIGS. 1 to 8 after it has been inserted into the intestine of a sheep.

In FIGS. 1 to 6 there is shown a re-entrant cannula device, comprising:

(a) a casing generally designated 1, of a non-toxic, resilient material, with a plug cock cavity 2 open at one side 4 to a frontal portion 6 of the casing 1 and an external, purse string groove 8 extending around an intermediate portion 10 of the plug cock cavity 2, the casing 1 having a frontal flange 12 bounding the open side 4 of the plug cock cavity 2 and extending laterally therefrom around the frontal portion 6 and being (as will be described later) for frontal retention of skin and abdominal wall, an inner, perforated flange 14, the inner flange 14 being inwardly spaced from the frontal portion 6 and extending laterally in the same direction as and substantially parallel to the frontal flange 12 and closer thereto than the purse string groove 8 and extending around the intermediate portion 10 of the plug cock cavity 2 for (as will be described later) adhesion to the internal side of the abdominal wall, and two intestine connectors 16 and 18 inwardly spaced from the purse string groove 8, the intestine connectors 16 and 18 being splayed and for conveying (as will be described later) intestine digesta to and from the plug cock cavity 2, (b) a cylindrical plug cock 22 (FIGS. 4 and 5), of a non-toxic material for pressing into the plug cock cavity 2 through the open side 4 thereof and being rotatably retained therein for rotation (as will be described later) about an axis XX extending across the plug cock cavity 2 between the two intestine connectors 16 and 18, the plug cock 22 having two intestine digesta conveying passages 24 and 26 extending therethrough along separate, isolated, curved paths for alignment with the two intestine connectors 16 and 18 so that (as will be described later) rotation of the plug cock 22 in the plug cock cavity 2 will position the plug cock 22 therein for, (i) in a first position the flow of digesta along only one of the passages 24 and 26 between the two intestine connectors 16 or 18 while one end of the other passage 24 or 26 is accessible through the open side 4 of the plug cock cavity 2, and (ii) in a second position the flow of digesta along one passage 24 or 26 from one of the intestine connectors 16 or 18 and the flow of digesta along the other passage 24 or 26 to the other intestine connector 16 or 18, and (c) two substantially rigid connector tubes, one of which is shown and designated 28 (FIG. 6) of a non-toxic material for placement (as will be described later) to extend through the open side 4 of the plug cock cavity 2 with end portions of the connector tube, such as 28 releasably secured in end portions of the passages 24 and 26 in the plug cock 22, at least one of which connector tubes, such as 28, may be used to rotate the plug cock 22 between the said first and second positions.

Preferably a closure cap 30 (FIGS. 7 and 8) of a non-toxic material and having a beaded 32 rim for (as will be described later) press-fitting over the frontal flange 12 to seal the plug cock cavity 2 is provided.

Prototypes of the casing 1 have been moulded of polyvinyl chloride marketed under the trademark PVC plastisol Type R-3703 by Reynolds Chemical Products Division, Ann Arbor, Mich., U.S.A. The open side 4 of the plug cock cavity 2 has two semi-circular, connector tube receiving grooves 34 and 36, and the plug cock cavity 2 is shaped a portion of a cylinder to closely fit the cylindrical plug cock 22 in the conventional manner.

The inner, perforated flange 14 is perforated by slots 38 spaced around it. The two intestine connectors 16 and 18 are each provided with two external, circumferential, securing grooves 40.

The cylindrical plug cock 22 has indents 42 in portions thereof forming ends of the passages 24 and 26 for securing the connector tubes, such as 28 by nipple 43, into the ends of passages 24 and 26.

The closure cap 30 is provided with a flap 44 to facilitate removal of the closure cap 30 from the frontal flange 12.

As shown in FIG. 9, in this embodiment an external collar 46, of a non-toxic material such as polyacrylamide, may be provided to be placed around the casing 1 between the frontal flange 12 and the skin when the cannula device is used. This is preferable when the abdominal wall of the sheep is thinner than 2 cm or there is a possibility that the frontal flange 12 may not provide sufficient surface area to prevent the frontal flange 12 from being pulled through an incision through which it has been passed.

Figure 11:
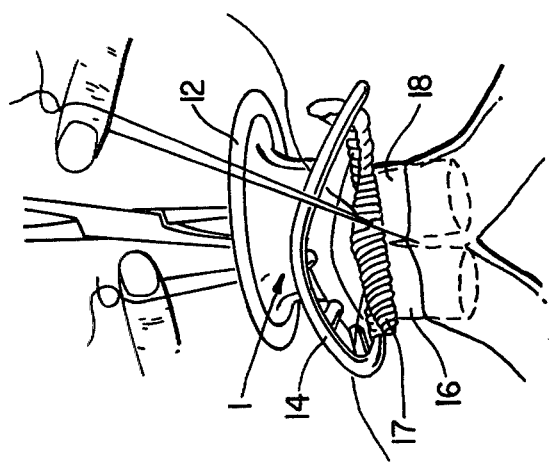
Figure 10:
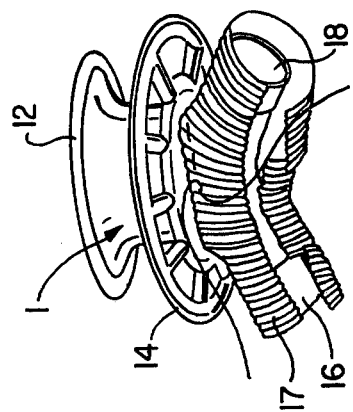

In FIGS. 10 to 12, similar parts to those shown in FIGS. 1 to 8 are designated by the same reference numerals and the previous description is relied upon to describe them.

Referring now to FIGS. 10 to 12, in the surgical procedure for the insertion of the device shown in FIGS. 1 to 8 in a sheep abdomen a 22 mm I.D. straight arterial graft 17 (65 cm usable length) of woven Dacron (Trademark) material obtainable as No. 00770 from USCI, Billerica Mass. U.S.A., was divided into 7 parts. Each part was then stretched to a 7 cm length and a 30 mm long×15 mm wide oval hole was cut out in the middle (2 cm from each end). The connectors 16 and 18 of the cannula device were inserted into the oval hole of the arterial graft with the aid of forceps (see FIG. 11). A purse string suture (size 2 silk thread) was placed into the graft around the casing 1 of the cannula device. The casing 1 with the arterial graft over the connectors 16 and 18, and the plug cock 22 were subjected to cold sterilization for at least 3 hours before surgery. Prior to insertion into the intestine the arterial graft was incised to form a shorter and longer side. An incision was also made into the longer side of the graft 2 cm from each end to from 3 parts (see FIG. 10).

More specifically, sheep (wethers) of approximately 40 kg liveweight, fasted for 24 hours before surgery, were injected intravenously with 4 ml/10 kg body weight of 60 mg/ml Nembutol (Trademark). The sheep were placed on an operating table and a light surgical anesthesia was maintained with halothane (1.5%), nitrous oxide (0.2 liter/min) and oxygen (0.4 liter/min). A lactated ringer's injection (Hartman Solution) with 5% Dextrose, obtainable from Baxter Laboratories Limited, Malton, Ontario, Canada, was infused intravenously into the sheep during surgery. The right paralumbar fossa was shaved and disinfected. The skin and abdominal wall were incised and approximately 15 cm of the intestine exteriorized. Two loops, 5 mm apart, of silk thread were attached to the antimesenteric side of the intestine, in the middle of the area to be used for insertion of the cannula device. A 5 cm incision was made along the stretched intestine, between the two loops. The casing 1, bent with the aid of forceps as shown in FIG. 11, was inserted into the incised intestine. During the insertion, an assistant held both thread-loops upward as shown in FIG. 11 in order to pull the intestine over the two intestine connectors 16 and 18 of the casing 1. The intestine was then pushed with fingers until both of the intestine connectors 16 and 18 rested inside the intestine and the forceps were released and pulled out of the casing 1. A sterile grease was applied over the cylindrical plug cock 22 which was immediately inserted into the casing 1 and adjusted into the "first position" described above. A purse string suture was placed into the intestine around the purse string groove 8 in the casing 1 using size 3/0 chromic catgut.

The three parts of the longer side of the arterial graft were inserted through the mesentery just under the intestinal wall and between blood vessels. The graft encircled the intestine which was stretched over the intestine connectors 16 and 18 of the casing 1. The two sides of the graft were then attached to each other using size 1 silk thread and continuous lockstitch (see FIG. 12); it was found that the arterial graft should not be fitted too tightly over the intestine. The two incision in the longer side of the arterial graft provided gaps through which the mesenteric blood vessels could enter the cannulated portion of the intestine and maintain blood circulation. The casing 1, without the cylindrical plug cock therein was exteriorized through a 3 cm incision in the skin and abdomen, with the aid of forceps.

The peritoneum and muscle were closed with chromic catgut (size 2/0 and 2 respectively) in a continuous lockstitch and the skin incision was closed with silk thread (size 2) in an interrupted suture.

The cylindrical plug cock 22 was removed from the casing 1 and the external collar 46 was placed around the casing 1 beneath the frontal flange 12 and then the plug cock 22, after re-greasing with a stopcock silicone grease, was inserted back into the casing 1 and adjusted to the "first position". A masking tape was then wrapped around the casing 1 and the external collar 46 in order to keep the external collar 46 in position.

The sheep were placed in a recovery room, and intramuscularly injected twice daily with 3 ml of penicillin on 3 consecutive days. Drinking water and the regular feeding were offered immediately after surgery. Healing appeared to be rapid and the skin sutures were removed on the 10th day after surgery.

In FIGS. 13 to 15, similar parts to those shown in FIGS. 1 to 5 are designated by the same reference numerals and the previous description is relied upon to describe them.

During the maintenance period when digesta is not collected, the cylindrical plug cock 22 is in the "first position" shown in FIG. 13 and allows an uninterrupted flow of digesta through the portion of the cannula device positioned inside the body of the sheep. The conversion of the cannula device from the "first position" shown in FIG. 13 to the re-entrant system "second position" shown in FIG. 15 is achieved by using the connector tube 28, which in tests was a seamless stainless steel tube (14.29 mm OD×35 mm×0.25 mm wall thickness), to rotate the cylindrical plug cock 22 in clockwise direction from the position shown in FIG. 13, through the position shown in FIG. 14 to the position shown in FIG. 15. A second stainless steel tube 48 (FIG. 15), identical to the connector tube 28, is then inserted in the intestine digesta passage 26 in the cylindrical plug cock 22 as a second connector tube. In the position shown in FIG. 15 the intestine digesta passage 26 in the cylindrical plug cock 22 diverts digesta externally and intestine digesta passage 24 allows subsequent return of digesta into the intestine. The two connector tubes 28 and 48 locate in the semicircular grooves 36 and 34 respectively to keep the cylindrical plug cock 22 in the proper position during the collection of digesta from the cannula and also serve as connectors to flexible plastic tubes during the collection and return of digesta. One end of each connector tube 28 and 48 is slashed (30°) and has the nipple 43 on the top which fits into recesses 42 in the cylindrical plug cock 22 to secure the connector tubes 28 and 48 in the cylindrical plug cock 22.

The external collar 46 was provided to tightly hold the casing 1 in the abdominal wall during the first 3 weeks after surgery. As tissue grew through the perforations 38 in the inner flange 14, the casing 1 became permanently attached to the internal side of the abdominal wall and adhered thereto so the external collar 46 was removed. The frontal flange 12 of the casing 1 then prevented an overgrowth of the casing 1 by the skin and provided an easy access to the cylindrical plug cock 22, in the casing 1. The intestine grows into the graft and this remains permanently attached to the cannula.

The closure cap 30 although not essential for successful maintenance of the casing 1 in sheep, provided protection for the cylindrical plug cock 22 and prevented the accumulation of dirt in the casing 1 during the flow of digesta as shown in FIG. 13. However, one sheep learned how to remove the closure cap 30 from the casing 1. If the closure cap 30 is not used a small piece of cloth should be inserted into the intestine digesta passage 24 of the cylindrical plug cock 22 to keep it clean.

No leakage of digesta around the casing 1 was apparent in any of the cannulated sheep for at least4 months; a very small leakage appeared in some sheep thereafter. There was however an endogenous secretion into the area over the intestinal tube of the two intestine connectors 16 and 18, indicating normal blood circulation in the cannulated part of the intestine. The secretion product and a body plasma exuded around the casing 1 to the outside of the body. It appeared as a leakage which was more noticeable during the first 2 weeks after the surgery than at later stages. It was also more evident around a casing 1 in the duodenal than around one in the ileal and the amount varied between sheep (this leakage should not be confused with the leakage of digesta). Because the casing 1 only extended a few millimeters over the skin the possibility of damage to the cannula device was virtually eliminated and no special housing for the cannulated sheep was required. The wool around the casing 1 was clipped every 3 weeks and the area was washed and disinfected with 0.2% Furasone (Trademark). Unscheduled inspections were made to examine the cannula devices for possible blockage by digesta. No blockage of either duodenal or ileal cannula devices was apparent in any sheep fed silages, however, some blockages were suspected in ileal cannula devices of sheep fed a purified diet. To prevent spillage of digesta around the casing 1 during the inspection a plastic or rubber sheet (approximately 15×25 cm) with an incision near the top was fitted over the cannula device before it was opened. The cannula devices were flushed with warm saline solution with a 50 ml plastic syringe. The syringe was modified by enlarging the diameter of the delivery hole. A narrow strip of masking tape was wrapped around the outlet of the syringe to make it fit tightly into the connectors 28 and 48. The connectors were inserted into passages 24 and 26 of the cylindrical plug cock 22 which was turned to the position shown in FIG. 15. If necessary, for a thorough cleaning of the cannula device or other purpose, the cylindrical plug cock 22 could be easily pulled out of the casing 1 with the aid of a string inserted into the passage 24 of the cylindrical plug cock 22 when the cylindrical plug cock 22 was in the position shown in FIG. 13.

The cannula device according to the present invention and the surgical procedure described above have been developed over a number of years; several sheep have been fitted with either one or two of the cannulas (proximal duodenum and terminal ileum) at different stages of development. The cannula devices have been utilized in a number of experiments.

Previous experience with a new type of cannula device developed by one of the applicants and described in "A New Method For Re-Entrant Cannulation Of The Duodenum In Sheep", M. Ivan, 1977, Canadian Journal of Animal Science, 57, pages 225 to 227, showed very rapid post-surgery recovery of cannulated sheep; the majority of cannulated sheep were eating a regular diet the day after surgery. This was probably due to the fact that re-entrant cannulation of this type did not require an intestinal transection and mesenteric incision under the transection in contrast to the methods used previously. Therefore, very little damage was done to the blood and nervous systems. Although this new type of cannula device was successfully used at the site of the proximal duodenum in sheep, its use at the site of terminal ileum was limited due to frequent blockages with the digesta during collection. This problem also occurred in the early stages of the development leading to the cannula device according to the present invention but was resolved when the cannula device according to the present invention was invented.

Cannula devices according to the present invention have also been used successfully in pigs, however, pigs were found to reject superpolyamide substances within approximately three to four months from implanting the cannula devices in them but this is within the useful time period that the cannula devices would be used.

We claim:

1. A re-entrant cannula device, comprising:
   (a) a casing, of a non-toxic, resilient material, with a plug cock cavity open at one side to a frontal portion of the casing and an external, purse string groove extending around an intermediate portion of the plug cock cavity, the casing having a frontal flange bounding the open side of the plug cock cavity and extending laterally therefrom around the frontal portion and being for frontal retention of skin and adbominal wall, an inner, perforated flange, the inner flange being inwardly spaced from the frontal portion and extending laterally in the same direction as and substantially parallel to the frontal flange and closer thereto than the purse string groove and extending around the intermediate portion of the plug cock cavity for subcutaneous adhesion to the internal side of the abdominal wall, and two intestine connectors inwardly spaced from the purse string groove, the intestine connectors being splayed and for conveying intestine digesta to and from the plug cock cavity.
   (b) a cylindrical plug cock, of a non-toxic material for pressing into the plug cock cavity through the open side thereof and being rotatably retained therein for rotation about an axis extending across the plug cock cavity between the two intestine connectors, the plug cock having two intestine digesta conveying passages extending therethrough along separate, isolated, curved paths for alignment with the two intestine connectors so that rotation of the plug cock in the plug cock cavity will position the plug cock therein for,
      (i) in a first position the flow of digesta along only one of the passages between the two intestine connectors while one end of the other passage is accessible through the open side of the plug cock cavity, and
      (ii) in a second position the flow of digesta along one passage from one of the intestine connectors and the flow of digesta along the other passage to the other intestine connector, and
   (c) two substantially rigid connector tubes of a non-toxic material for placement to extend through the open side of the plug cock cavity with end portions of the connector tube releasably secured in end portions of the passages in the plug cock, at least one of which connector tubes may be used to rotate the plug cock between the said first and second positions.

2. A device according to claim 1, further comprising a closure cap of a non-toxic material and having a beaded rim for press-fitting over the frontal flange to seal the plug cock cavity.

3. A device according to claim 1, further comprising an external collar for placement around the casing between the frontal flange and skin when the device is in use.

* * * * *